(12) United States Patent
Kutsukake et al.

(10) Patent No.: US 10,335,509 B2
(45) Date of Patent: Jul. 2, 2019

(54) PRESSURE-SENSITIVE ADHESIVE AGENT FOR SKIN, PRESSURE-SENSITIVE ADHESIVE SHEET FOR SKIN, AND FACE PLATE OF OSTOMY APPLIANCE

(75) Inventors: Yumi Kutsukake, Tokyo (JP); Takabumi Kubo, Tokyo (JP); Shigeyoshi Nakamura, Tokyo (JP)

(73) Assignee: ALCARE CO., LTD., Tokyo (JP)

( * ) Notice: Subject to any disclaimer, the term of this patent is extended or adjusted under 35 U.S.C. 154(b) by 415 days.

(21) Appl. No.: 12/808,593

(22) PCT Filed: Dec. 18, 2008

(86) PCT No.: PCT/JP2008/073065
§ 371 (c)(1),
(2), (4) Date: Jun. 16, 2010

(87) PCT Pub. No.: WO2009/087877
PCT Pub. Date: Jul. 16, 2009

(65) Prior Publication Data
US 2011/0130698 A1   Jun. 2, 2011

(30) Foreign Application Priority Data
Jan. 10, 2008 (JP) ................................ 2008-003200

(51) Int. Cl.
| | | |
|---|---|---|
| *A61F 15/00* | (2006.01) | |
| *A61L 15/58* | (2006.01) | |
| *A61L 15/44* | (2006.01) | |
| *A61L 24/00* | (2006.01) | |
| *A61L 24/04* | (2006.01) | |
| *A61F 13/02* | (2006.01) | |

(52) U.S. Cl.
CPC ........ *A61L 15/585* (2013.01); *A61F 13/0253* (2013.01); *A61F 13/0256* (2013.01); *A61L 15/44* (2013.01); *A61L 24/0015* (2013.01); *A61L 24/043* (2013.01); *A61L 2300/22* (2013.01)

(58) Field of Classification Search
CPC .. A61F 13/02; A61F 13/0256; A61F 13/0253; A61L 15/44; A61L 24/0015; A61L 24/043; A61L 15/585; A61L 2300/22
USPC ..................... 602/54, 56; 604/277
See application file for complete search history.

(56) References Cited

U.S. PATENT DOCUMENTS

| | | | | |
|---|---|---|---|---|
| 3,953,293 A | * | 4/1976 | Horii et al. ................... 435/82 |
| 4,147,831 A | * | 4/1979 | Balinth ................ A61L 15/585 |
| | | | | 428/356 |
| 4,178,407 A | * | 12/1979 | Rubens ................. A41D 31/02 |
| | | | | 428/297.1 |
| 4,192,785 A | * | 3/1980 | Chen et al. ................... 523/118 |
| 4,200,080 A | * | 4/1980 | Cook ................... F02N 11/0803 |
| | | | | 123/179.16 |
| 4,204,540 A | * | 5/1980 | Cilento et al. ................. 604/336 |
| 4,231,369 A | * | 11/1980 | Sorensen et al. .............. 604/336 |
| 4,253,460 A | * | 3/1981 | Chen et al. ..................... 604/336 |
| 4,393,080 A | * | 7/1983 | Pawelchak et al. ....... 428/355 R |
| 4,486,195 A | * | 12/1984 | Weinstein .............. C11D 1/528 |
| | | | | 510/328 |
| 4,505,976 A | * | 3/1985 | Doehnert et al. ........ 428/355 CP |
| 4,551,490 A | | 11/1985 | Doyle et al. |
| 5,147,698 A | * | 9/1992 | Cole ........................... 428/41.3 |
| 5,462,681 A | * | 10/1995 | Gutzmann ........... C10M 173/02 |
| | | | | 508/513 |
| 5,492,943 A | * | 2/1996 | Stempel ........................ 523/111 |
| 5,591,792 A | * | 1/1997 | Hattori et al. ................. 524/271 |
| 5,827,528 A | * | 10/1998 | Kubo et al. ................... 424/443 |
| 6,146,654 A | * | 11/2000 | Kubo ............................ 424/443 |
| 6,149,924 A | * | 11/2000 | Paul ............................. 424/401 |
| 6,171,594 B1 | * | 1/2001 | Nielsen ......................... 424/744 |
| 6,326,421 B1 | * | 12/2001 | Lipman ........................... 524/22 |

(Continued)

FOREIGN PATENT DOCUMENTS

| | | |
|---|---|---|
| JP | 54-13693 A | 2/1979 |
| JP | 60-20976 A | 2/1985 |

(Continued)

OTHER PUBLICATIONS

Ferrari et al. International Journal o Pharmaceutics 117, 1995, 49-55.*

(Continued)

*Primary Examiner* — Alexander C Kollias
(74) *Attorney, Agent, or Firm* — Birch, Stewart, Kolasch & Birch, LLP (57) ABSTRACT

[Objective]
To provide a pressure-sensitive adhesive agent for skin containing a pressure-sensitive adhesive agent for skin that has favorable shape retention properties and skin-follow up properties without being adversely affected by moisture from excrement or the like even when adhered to the skin over a long period of time and yet leaves no adhesive residue after separation and a pressure-sensitive adhesive sheet for skin contains a base material and a layer of the pressure-sensitive adhesive agent for skin.
[Means to Achieve Objectives]
A pressure-sensitive adhesive agent for skin contains 2 to 35% by weight of a thermoplastic elastomer, 25 to 60% by weight of a hydrophilic polymer compound, 16 to 40% by weight of a softener, and 0.01 to 4.8% by weight of a physiologically active agent; and has a water absorption 3 hours after of 55 to 240% and a water absorption 24 hours after of 240 to 450%. A pressure-sensitive adhesive sheet for skin contains a base material and a layer of a pressure-sensitive adhesive agent for skin that contains 2 to 35% by weight of a thermoplastic elastomer, 25 to 60% by weight of a hydrophilic polymer compound, 16 to 40% by weight of a softener, and 0.01 to 4.8% by weight of a physiologically active agent and is formed on one side of the base material; and has a water absorption 3 hours after of 55 to 240% and a water absorption 24 hours after of 240 to 450%.

16 Claims, 1 Drawing Sheet

(56) References Cited

U.S. PATENT DOCUMENTS

| | | | |
|---|---|---|---|
| 6,437,038 B1 * | 8/2002 | Chen | 524/474 |
| 6,437,039 B1 * | 8/2002 | Ahmed | C09D 183/04 524/261 |
| 6,451,883 B1 * | 9/2002 | Chen et al. | 524/31 |
| 6,558,792 B1 * | 5/2003 | Vaabengaard et al. | 428/355 CP |
| 6,576,712 B2 * | 6/2003 | Feldstein et al. | 525/326.9 |
| 6,583,220 B1 * | 6/2003 | Lipman | 525/54.3 |
| 6,673,056 B2 * | 1/2004 | Metz et al. | 604/338 |
| 6,710,100 B1 * | 3/2004 | Lipman | 523/111 |
| 6,740,711 B1 * | 5/2004 | Lipman et al. | 525/216 |
| 6,815,058 B2 * | 11/2004 | Watanabe et al. | 428/354 |
| 6,902,551 B2 * | 6/2005 | Hansen et al. | 604/342 |
| 6,958,154 B2 * | 10/2005 | Andolino Brandt et al. | 424/400 |
| 7,029,464 B2 * | 4/2006 | Fenton | 604/338 |
| 7,347,844 B2 * | 3/2008 | Cline et al. | 604/337 |
| 7,651,485 B2 * | 1/2010 | Fattman | 604/344 |
| 7,771,735 B2 * | 8/2010 | Dvoracek et al. | 424/404 |
| 7,857,796 B2 * | 12/2010 | Cline et al. | 604/338 |
| 7,867,207 B2 * | 1/2011 | Therkelsen et al. | 604/342 |
| 7,976,522 B2 * | 7/2011 | Hansen et al. | 604/338 |
| 8,076,528 B2 * | 12/2011 | Lam et al. | 602/56 |
| 2002/0013249 A1 * | 1/2002 | Nakagawa | A61K 8/0208 510/384 |
| 2004/0030315 A1 * | 2/2004 | Brooks | 604/382 |
| 2004/0102744 A1 * | 5/2004 | Fattman | 604/344 |
| 2004/0138177 A1 * | 7/2004 | Park et al. | 514/78 |
| 2004/0193122 A1 * | 9/2004 | Cline et al. | 604/332 |
| 2004/0241215 A1 * | 12/2004 | Lipman | 424/445 |
| 2004/0241246 A1 * | 12/2004 | Lipman | 424/486 |
| 2005/0182443 A1 * | 8/2005 | Jonn et al. | 606/213 |
| 2005/0281869 A1 * | 12/2005 | Kruse et al. | 424/449 |
| 2007/0083139 A1 * | 4/2007 | Tsuruda et al. | 602/54 |
| 2007/0156076 A1 * | 7/2007 | Jackson et al. | 602/54 |
| 2007/0179461 A1 * | 8/2007 | Sambasivam et al. | 604/336 |
| 2007/0243353 A1 * | 10/2007 | Kubo | 428/40.1 |
| 2008/0009779 A1 * | 1/2008 | Fabo et al. | 602/42 |
| 2008/0051743 A1 * | 2/2008 | Falconer et al. | 604/332 |
| 2009/0076542 A1 * | 3/2009 | Jonn et al. | 606/215 |
| 2009/0214628 A1 * | 8/2009 | de Rijk | 424/450 |
| 2009/0306571 A1 * | 12/2009 | Lam et al. | 602/56 |
| 2010/0113999 A1 * | 5/2010 | Lam et al. | 602/79 |
| 2010/0280429 A1 * | 11/2010 | Bach et al. | 602/54 |
| 2011/0251542 A1 * | 10/2011 | Buus et al. | 602/54 |

FOREIGN PATENT DOCUMENTS

| | | | | |
|---|---|---|---|---|
| JP | 62-47545 B2 | 10/1987 | | |
| JP | 5-123389 A | 5/1993 | | |
| JP | 6-200 A | 1/1994 | | |
| JP | 6-14957 B2 | 3/1994 | | |
| JP | 6-78507 B2 | 10/1994 | | |
| JP | 8-722 A | 1/1996 | | |
| JP | 2947728 B2 | 9/1999 | | |
| JP | 2002-17765 A | 1/2002 | | |
| JP | 3471122 B2 | 11/2003 | | |
| JP | 2004-305725 A | 11/2004 | | |
| JP | 2006-263042 A | 10/2006 | | |
| WO | WO 9911728 A1 * | 3/1999 | | C09J 153/02 |

OTHER PUBLICATIONS

STN Search Report, pp. 1-4.*

English language translation of Jp 2006-263042, pp. 1-9.*

JSR DYNARON—Hydrogenated Polymer, JSR corporation, pp. 1-8, no publication date given.*

Kraton G SEBS and SPES Polymers—Kraton, pp. 1-2, no publication date given.*

STN Search Report, pp. -13, Feb. 6, 2017.*

Kraton G (SEBS, SEP, SEPS), p. 1, no publication data given, obtained online from: http://www.boundarybayenterprises.com/files/Kraton_G.pdf.*

Satoru Numata et al., "Ceramide Gan'yu Hifu Hogozai ni yoru Stoma Dogu Chofubu Hifu no Barrier Kino Kaizen Koka", Journal of Japanese Society of Stoma and Continence Rehabilitation, Jun. 25, 2007 (Jun. 25, 2007), vol. 23, No. 2, pp. 9 to 19, ISSN: 1882-0115.

Satoru Numata et al., "Shinki Skin care Seibun (Ceramide) o Haigo shita Hifu Hogozai no Yuyosei (the 1st report)", Journal of Japanese Society of Stoma Rehabilitation, Dec. 2004, vol. 20, No. 3, pp. 77, 073, ISSN: 0916-6440.

Satoru Numata et al., "Shinki Skin care Seibun (Ceramide) o Haigo shita Hifu Hogozai no Yuyosei (the 2nd report)", Journal of Japanese Society of Stoma Rehabilitation, Dec. 2004, vol. 20, No. 3, pp. 77, 074, ISSN: 0916-6440.

* cited by examiner

# PRESSURE-SENSITIVE ADHESIVE AGENT FOR SKIN, PRESSURE-SENSITIVE ADHESIVE SHEET FOR SKIN, AND FACE PLATE OF OSTOMY APPLIANCE

TECHNICAL FIELD

The present invention relates to a pressure-sensitive adhesive agent for skin, a pressure-sensitive adhesive sheet for skin, and a face plate of ostomy appliance.

More specifically, the present invention relates to a pressure-sensitive adhesive agent for skin for use in protection of the skin surrounding a stoma, a face plate of ostomy appliance, wound bandages, and the like, a pressure-sensitive adhesive sheet having a layer of the pressure-sensitive adhesive agent for skin, and a face plate of ostomy appliance having the pressure-sensitive adhesive sheet for skin.

BACKGROUND ART

For persons who cannot control excretion of feces or urine by their will or persons with diseases of organs of the digestive system or the urinary system, a surgical operation is performed to draw the intestinal tract or the ureter to the body surface to form an opening referred to as a stoma on the body surface. In this case, persons with a stoma (hereinafter sometimes referred to as a "stoma holder") need to have an ostomy appliance capable of temporarily storing excrement from the stoma attached to the surrounding of the stoma. The ostomy appliance contains a pouch for storing excrement and a pressure-sensitive adhesive sheet referred to as a face plate and is used by adhering and fixing the face plate to the surrounding of the stoma.

For the face plate of the ostomy appliance, a so-called hydrocolloid pressure-sensitive adhesive agent for skin containing hydrophilic polymer compounds is generally used so as to absorb the moisture from the skin or excrement even when adhered to the skin over a long period of time (e.g., Patent Documents 1 to 9).

It is also important for the face plate of the ostomy appliance to maintain the balance of aggregation properties, shape retention properties, and skin-follow up properties in addition to satisfying the water absorption properties.

Some former face plates can absorb much moisture, but the aggregation properties are not sufficient. Thus, a pressure-sensitive adhesive agent for skin has leaked out from the outer peripheral edge of the face plate after water absorption or an adhesive residue has been left after separation in some cases. Former face plates having increased aggregation properties or shape retention properties have poor water absorption properties or skin-follow up properties in some cases, and thus the face plate has separated when adhered over a long period of time or unpleasantness has arisen during adhesion in some cases.

Moreover, since the stoma holders use the ostomy appliance over a long term, the physiological function (skin barrier function) of the skin decreases to easily cause dermatitis or the like due to repeated adhering and separating of the face plate.

The pressure-sensitive adhesive agent for skin or pressure-sensitive adhesive sheet for skin for use in wound bandages or the like has also been desired to promptly absorb the blood, exudate, or the like, have favorable adaptability to the diseased part when adhered over a long period of time, and leave no adhesive residue after separation.

[Patent Document 1] Japanese Examined Patent Application Publication No. 6-14957
[Patent Document 2] Japanese Patent No. 2947728
[Patent Document 3] Japanese Examined Patent Application Publication No. 62-47545
[Patent Document 4] Japanese Patent No. 3471122
[Patent Document 5] Japanese Unexamined Patent Application Publication No. 6-200
[Patent Document 6] Japanese Unexamined Patent Application Publication No. 5-123389
[Patent Document 7] Japanese Examined Patent Application Publication No. 6-78507
[Patent Document 8] Japanese Unexamined Patent Application Publication No. 2004-305725
[Patent Document 9] Japanese Unexamined Patent Application Publication No. 2006-263042

DISCLOSURE OF THE INVENTION

Technical Problems to be Solved

Accordingly, it is an object of the present invention to provide a pressure-sensitive adhesive agent for skin that has favorable shape retention properties and skin-follow up properties without being adversely affected by the moisture from excrement or the like even when adhered to the skin over a long period of time and yet leaves no adhesive residue after separation.

It is another object of the invention to provide a pressure-sensitive adhesive agent for skin that may maintain or increase the physiological function (skin barrier function) of the skin.

It is still another object of the invention to provide a pressure-sensitive adhesive sheet for skin containing a base material and a layer of the pressure-sensitive adhesive agent for skin.

It is still another object of the invention to provide a face plate of ostomy appliance having the pressure-sensitive adhesive sheet for skin.

Means to Solve the Problems

Thus, the invention provides a pressure-sensitive adhesive agent for skin, containing: 2 to 35% by weight of a thermoplastic elastomer, 25 to 60% by weight of a hydrophilic polymer compound, 16 to 40% by weight of a softener, and 0.01 to 4.8% by weight of a physiologically active agent; and having a water absorption 3 hours after of 55 to 240% and a water absorption 24 hours after of 240 to 450%.

In the pressure-sensitive adhesive agent for skin of the invention, the physiologically active agent is preferably a hydrophilic physiologically active agent.

In the pressure-sensitive adhesive agent for skin of the invention, the physiologically active agent is preferably a sphingolipid.

In the pressure-sensitive adhesive agent for skin of the invention, the thermoplastic elastomer is preferably a hydrogenated styrene-butadiene rubber.

The pressure-sensitive adhesive agent for skin of the invention preferably further contains 1 to 30% by weight of oil.

The pressure-sensitive adhesive agent for skin of the invention preferably further contains 1 to 25% by weight of a tackifying resin.

When such a specific composition of the invention and given water absorption properties based on the composition are combined, favorable adhesiveness or adaptability to the skin is demonstrated, and an adhesive residue or separation irritation is prevented, and thus the physiological function of the skin can be maintained or increased.

A pressure-sensitive adhesive agent for skin of the invention preferably contains: 2 to 35% by weight of a styrene thermoplastic elastomer, 25 to 60% by weight of at least one hydrophilic polymer compound selected from the group consisting of sodium carboxymethylcellulose, pectin, karaya gum, and gelatin, 16 to 40% by weight of at least one softener selected from the group consisting of polyisobutylene, polyisoprene, polybutadiene, polybutene, styrene-isoprene rubber, ethylene-propylene rubber, styrene-ethylene-propylene rubber, and derivatives thereof, 0.01 to 4.8% by weight of a physiologically active agent, 1 to 30% by weight of oil, and 1 to 25% by weight of a tackifying resin; and has a water absorption 3 hours after of 55 to 240% and a water absorption 24 hours after of 240 to 450%.

The invention provides a pressure-sensitive adhesive sheet for skin, containing: a base material and a layer of a pressure-sensitive adhesive agent for skin that contains 2 to 35% by weight of a thermoplastic elastomer, 25 to 60% by weight of a hydrophilic polymer compound, 16 to 40% by weight of a softener, and 0.01 to 4.8% by weight of a physiologically active agent and is formed on one side of the base material; and having a water absorption 3 hours after of 55 to 240% and a water absorption 24 hours after of 240 to 450%.

In the pressure-sensitive adhesive sheet for skin of the invention, the physiologically active agent is preferably a hydrophilic physiologically active agent.

In the pressure-sensitive adhesive sheet for skin of the invention, the physiologically active agent is preferably a sphingolipid.

In the pressure-sensitive adhesive sheet for skin of the invention, the thermoplastic elastomer is preferably a hydrogenated styrene-butadiene rubber.

The pressure-sensitive adhesive sheet for skin of the invention preferably further contains 1 to 30% by weight of oil.

The pressure-sensitive adhesive sheet for skin of the invention preferably further contains 1 to 25% by weight of a tackifying resin.

A pressure-sensitive adhesive sheet for skin of the invention preferably contains: a base material and a layer of a pressure-sensitive adhesive agent for skin that contains 2 to 35% by weight of a thermoplastic elastomer, 25 to 60% by weight of at least one hydrophilic polymer compound selected from the group consisting of sodium carboxymethylcellulose, pectin, karaya gum, and gelatin, 16 to 40% by weight of at least one softener selected from the group consisting of polyisobutylene, polyisoprene, polybutadiene, polybutene, styrene-isoprene rubber, ethylene-propylene rubber, styrene-ethylene-propylene rubber, and derivatives thereof, 0.01 to 4.8% by weight of a physiologically active agent, 1 to 30% by weight of oil, and 1 to 25% by weight of a tackifying resin and is formed on one side of the base material; and has a water absorption 3 hours after of 55 to 240% and a water absorption 24 hours after of 240 to 450%.

The invention provides a pressure-sensitive adhesive sheet for face plate of ostomy appliance containing the pressure-sensitive adhesive sheet for skin of the invention.

The pressure-sensitive adhesive sheet for face plate of ostomy appliance of the invention preferably has a convex shape on the surface adhering to the skin of the layer of the pressure-sensitive adhesive agent for skin.

It is preferable in the pressure-sensitive adhesive sheet for face plate of ostomy appliance of the invention that a stoma inserting hole be formed in the central part and the base material be not present in the surrounding of the hole.

It is preferable in the pressure-sensitive adhesive sheet for face plate of ostomy appliance of the invention that a stoma inserting hole be formed in the central part and the base material surrounding the hole have a fragile portion.

The invention provides a face plate of ostomy appliance containing the pressure-sensitive adhesive sheet for face plate of ostomy appliance of the invention.

Effects of the Invention

The pressure-sensitive adhesive agent for skin of the invention has favorable adhesiveness or adaptability to the skin, maintains sufficient absorption properties of sweat, moisture from excrement, and the like and shape retention properties after absorption, leaves no pressure-sensitive adhesive agent for skin after separation, and can be separated without applying damages to the skin or the wound surface.

Accordingly, the pressure-sensitive adhesive sheet for skin using the pressure-sensitive adhesive agent for skin and the face plate for ostomy containing the pressure-sensitive adhesive sheet for skin causes no skin irritation or unpleasantness even when adhered to the skin over a long period of time and are hardly separated from the skin due to the influence of excrement or moisture.

BEST MODES FOR CARRYING OUT THE INVENTION (Pressure-Sensitive Adhesive Agent for Skin)

A pressure-sensitive adhesive agent for skin of the invention contains a thermoplastic elastomer, a hydrophilic polymer compound, a softener, and a physiologically active agent.

(Thermoplastic Elastomer)

Specific examples of a thermoplastic elastomer for constituting the pressure-sensitive adhesive agent for skin of the invention include a styrene thermoplastic elastomer, an olefin thermoplastic elastomer, a polyester thermoplastic elastomer, a polyamide thermoplastic elastomer, a urethane thermoplastic elastomer, a vinyl chloride thermoplastic elastomer, and a diene thermoplastic elastomer.

Among the above, the styrene thermoplastic elastomer is suitable.

Specific examples of the styrene thermoplastic elastomer include a hydrogenated styrene-butadiene rubber (HSBR), a styrene-isoprene-styrene block copolymer (SIS), a styrene-butadiene-styrene block copolymer (SBS), a styrene-ethylene/propylene-styrene block copolymer (SEPS), a styrene-ethylene/butylene-styrene block copolymer (SEBS), a styrene-ethylene/ethylene/propylene-styrene block copolymer (SEEPS), and a styrene-ethylene/butylene-olefin crystal block copolymer (SEBC).

Among the above, the hydrogenated styrene butadiene rubber (HSBR) and the styrene-isoprene-styrene block copolymer (SIS) are preferable and the hydrogenated styrene butadiene rubber (HSBR) is particularly preferable.

In the invention, the thermoplastic elastomer may be used singly or in combination of two or more kinds thereof.

The blending amount of the thermoplastic elastomer needs to be 2 to 35% by weight relative to the whole weight of the pressure-sensitive adhesive agent for skin. The blending amount thereof is preferably 5 to 20% by weight.

Since the blending amount of the thermoplastic elastomer is within the above-mentioned range, the aggregation properties and the shape retention properties of the pressure-sensitive adhesive agent for skin increase, and thus excessive swelling of the pressure-sensitive adhesive agent for skin, the flow (collapse) of the pressure-sensitive adhesive agent for skin after water absorption, and leaving an adhesive residue after separation can be prevented.

(Hydrophilic Polymer Compound)

As hydrophilic polymer compounds for constituting the pressure-sensitive adhesive agent for skin of the invention, natural, semi-synthetic, or synthetic hydrophilic polymer compounds can be used.

Specific examples of the natural hydrophilic polymer compounds include plant polymers, such as gum arabic, tragacanth gum, galactan, guar gum, carob gum, karaya gum, carragheenan, pectin, agar, or starch (e.g., starch of rice, corn, potato, or wheat); microbial polymers, such as xanthan gum, dextrin, dextran, succinoglucan, or pullulan; and animal polymers; such as casein, albumin, or gelatin.

Specific examples of the semi-synthetic hydrophilic polymer compounds include starch polymers (e.g., carboxy methyl starch and methyl hydroxy propyl starch, etc.); cellulose polymers (e.g., methylcellulose, ethylcellulose, methyl hydroxy propyl cellulose, hydroxyethylcellulose, cellulose sodium sulfate, hydroxy propyl cellulose, carboxymethylcellulose, and sodium carboxymethylcellulose, etc.); alginic acid polymers (e.g., sodium alginate and propylene glycol alginate, etc.).

Specific examples of the synthetic hydrophilic polymer compounds include vinyl polymers (e.g., polyvinyl alcohol, polyvinyl methyl ether, polyvinyl pyrrolidone, and carboxy vinyl polymer, etc.); and acrylic polymers (e.g., sodium polyacrylate, polyacrylamide, and polyethyleneimine, etc.).

Among these hydrophilic polymer compounds, sodium carboxymethylcellulose, pectin, karaya gum, and gelatin are preferable and sodium carboxymethylcellulose is particularly preferable.

In the invention, the hydrophilic polymer compounds may be used singly or in combination of two or more kinds thereof.

The blending amount of the hydrophilic polymer compounds needs to be 25 to 60% by weight relative to the whole weight of the pressure-sensitive adhesive agent for skin. The blending amount thereof is preferably 35 to 55% by weight. Since the blending amount of the hydrophilic polymer compounds is within the above-mentioned range, absorption of sweat or moisture of excrement by the pressure-sensitive adhesive agent for skin becomes favorable and skin irritation due to skin maceration or the like is reduced, and thus the pressure-sensitive adhesive agent for skin can be adhered to the skin over a long period of time.

(Softener)

As softeners for constituting the pressure-sensitive adhesive agent for skin of the invention, a liquid or semi-solid resin can be used. Specific examples of the softeners include polyisobutylene, polyisoprene, polybutadiene, polybutene, styrene-isoprene rubber, ethylene-propylene rubber, styrene-ethylene-propylene rubber, and derivatives of hydrogenated substances thereof. Among the above, polyisobutylene is suitable.

In the invention, the softeners may be used singly or in combination of two or more kinds thereof.

The blending amount of the softeners needs to be 16 to 40% by weight relative to the whole weight of the pressure-sensitive adhesive agent for skin. The blending amount is more preferably 20 to 40% by weight.

Since the blending amount of the softeners is within the above-mentioned range, the adhesion strength or softness of the pressure-sensitive adhesive agent for skin increases, and thus skin tension, physical stimuli due to the hardness of the pressure-sensitive adhesive agent for skin, and the like are eased.

(Physiologically Active Agent)

Physiologically active agents for constituting the pressure-sensitive adhesive agent for skin of the invention have a function of maintaining or increasing the physiological functions (skin barrier function and the like) of the skin. The physiologically active agents are not particularly limited, and preferably have hydrophilic groups, such as a hydroxy group, a carboxy group, an amino group, a carbonyl group, and a sulfo group and demonstrate hydrophilicity.

Specific examples of hydrophilic physiologically active agents include sphingolipid, urea, glycolic acid, amino acids (arginine, cystein, glycine, ricin, proline, serine, and the like) and derivatives thereof, protein hydrolysates (collagen, elastin, keratin, and the like), mucopolysaccharides (hyaluronic acid, chondroitin sulfate, heparin, etc.) and derivatives thereof, a vitamin B group (thiamin, riboflavin, nicotinic acid, pyridoxine, pyridoxal, pyridoxamine, biotin, folic acid, cyanocobalamin, and the like), ascorbic acids (vitamin C and derivatives thereof), retinoids (vitamin A, retinal, retinoic acid, and the like), Vitamin D (D2, D3, and the like), vitamin E and derivatives thereof, carotenoids (carotene, lycopene, xanthophyll, and the like), enzymes, coenzymes, and γ-oryzanol. Among the above, sphingolipid is particularly preferable.

As the sphingolipid, ceramide in which sphingosine and fatty acid are combined and sphingoglycolipid in which ceramide and sugar are combined are preferable.

As the ceramide, any of natural or synthetic ceramides may be used and ceramides of Types 1 to 7 can be mentioned, and the ceramides of Types 2, 5, and 7 are particularly preferable.

As the sphingoglycolipid, cerebroside, galactosyl ceramide, glucosyl ceramide, and the like are preferable.

In the invention, the physiologically active agents may be used singly or in combination of two or more kinds thereof.

The blending amount of the physiologically active agents needs to be 0.01 to 4.8% by weight relative to the whole weight of the pressure-sensitive adhesive agent for skin. The blending amount is preferably 0.05 to 3% by weight.

Since the blending amount of the physiologically active agent is within the above-mentioned range, the maintenance and improvement effects of the physiological functions (skin barrier function and the like) of the skin become excellent.

In particular, by the use of the hydrophilic physiologically active agents, the water absorption properties in a short time after adhesion become favorable and preferable water absorption properties of the invention are demonstrated when the hydrophilic physiologically active agents and other ingredients constituting the pressure-sensitive adhesive agent for skin of the invention are combined.

(Oil)

The pressure-sensitive adhesive agent for skin of the invention preferably contains oil in addition to the essential ingredients described above.

The usable oils may be any of mineral oils, vegetable oils, animal oils, and synthetic oils.

Specific examples of the mineral oils include liquid paraffin, liquid isoparaffin, and naphthene oil.

Specific examples of the vegetable oils include olive oil, olive squalane, macadamia nuts oil, jojoba oil, castor oil, coconut oil, palm oil, safflower oil, sunflower seed oil, hardened coconut oil, hardened palm oil, almond oil, peanut oil, cottonseed cake oil, avocado oil, apricot-kernel oil, grape seed oil, peppermint oil, mint oil, spearmint oil, lavender oil, tea tree oil, eucalyptus oil, Japanese mint oil, clove oil, cinnamon oil, rosemary oil, orange oil, lemongrass oil, lemon oil, yuzu citron oil, lime oil, grapefruit oil, and cypress oil.

Specific examples of the animal oils include lanolin, turtle oil, yellow beeswax, squalene, and pristane.

Specific examples of the synthetic oils include fatty acid triglyceride, such as glycerol-tri-2-ethylhexanoate; silicone oils, such as poly methyl phenyl siloxane, poly dimethyl siloxane, or amino silicon; and fatty acid esters, such as isopropyl myristate, octyldodecyl myristate, isononyl isononanate, isopropyl palmitate, or ethylhexyl palmitate.

Among the above, mineral oils are preferable and liquid paraffin is particularly preferable.

In the invention, the oils may be used singly or in combination of two or more kinds thereof.

The blending amount of the oils is preferably 1 to 30% by weight and more preferably 2 to 20% by weight relative to the whole weight of the pressure-sensitive adhesive agent for skin.

By blending the oils to the pressure-sensitive adhesive agent for skin, the softness and use feeling thereof can be improved and separation irritation can be reduced.

(Tackifying Resin)

The pressure-sensitive adhesive agent for skin of the invention preferably further contains a tackifying resin in addition to the essential ingredients described above.

Specific examples of usable adhesiveness-imparting resins include petroleum resins, such as aliphatic copolymers, aromatic copolymers, aliphatic-aromatic copolymers, or alicyclic copolymers; coumarone-indene resins; terpene resins; terpene-phenol resins; rosin resins such as polymerized rosin; (alkyl) phenol resin; xylene resin; and hydrogenated resins thereof.

In the invention, the adhesiveness-imparting resins may be used singly or in combination of two or more kinds thereof.

The blending amount of the adhesiveness-imparting resins is preferably 1 to 25% by weight and more preferably 5 to 20% by weight relative to the whole weight of the pressure-sensitive adhesive agent for skin.

By blending the adhesiveness-imparting resin to the pressure-sensitive adhesive agent for skin, even when the pressure-sensitive adhesive agent for skin is adhered to the skin over a long period of time, separation due to moisture contained in excrement or the like can be reduced and the adhesiveness to the skin improves.

(Other Ingredients)

Moreover, to the pressure-sensitive adhesive agent for skin of the invention, surfactants, powder, pH adjusters, antimicrobial agents, and the like can be blended as appropriate insofar as the objects of the invention are not impaired.

In the pressure-sensitive adhesive agent for skin of the invention, the water absorption 3 hours after and the water absorption 24 hours after need to be 55 to 240% and 240 to 450%, respectively, and preferably 60 to 200% and 250 to 420%, respectively. Since the water absorption is within the above-mentioned range, sweat or excrement is promptly absorbed and the deformation or leaving an adhesive residue during water absorption or separation is prevented. As a result, skin troubles when adhered decrease to maintain or increase the physiological function (skin barrier function) of the skin, and thus prolonged adhering can be achieved. The given water absorption of the invention closely relating to such suitable properties can be developed by combining the above-mentioned thermoplastic elastomers, hydrophilic polymer compounds, softeners, physiologically active agents, oils, adhesiveness-imparting resins, and the like at a given ratio.

In the pressure-sensitive adhesive agent for skin of the invention, the swelling ratio 3 hours after is preferably 135% or lower and the swelling ratio 24 hours after is preferably 145% or lower. Since the swelling ratio is within the above-mentioned range, the pressure-sensitive adhesive agent for skin can maintain the shape even after water absorption and leaves no adhesive residue even after separation.

The pressure-sensitive adhesive agent for skin of the invention preferably has a flexibility of 10 to 50 mm/20 mm. Since the flexibility is within the above-mentioned range, skin-follow up properties are high and unpleasantness hardly arises during adhesion.

The pressure-sensitive adhesive agent for skin of the invention has a visible light transmittance of preferably 2.5% or more and more preferably 5.0% or more. Since the visible light transmittance is within the above-mentioned range, the appearance when the pressure-sensitive adhesive agent for skin is adhered to the skin improves and the state of water absorption or the skin can be easily observed while the pressure-sensitive adhesive agent for skin is being adhered to the skin. Thus, a suitable time for replacement can be confirmed without separating the adhered pressure-sensitive adhesive agent for skin and leakage of moisture or unnecessary replacement can be prevented.

As a preferable aspect of the pressure-sensitive adhesive agent for skin of the invention, a pressure-sensitive adhesive agent for skin can be mentioned that contains 2 to 35% by weight of a styrene thermoplastic elastomer, 25 to 60% by weight of at least one hydrophilic polymer compound selected from the group consisting of sodium carboxymethylcellulose, pectin, karaya gum, and gelatin, 16 to 40% by weight of at least one softener selected from the group consisting of polyisobutylene, polyisoprene, polybutadiene, polybutene, styrene-isoprene rubber, ethylene-propylene rubber, styrene-ethylene-propylene rubber, and derivatives thereof, 0.01 to 4.8% by weight of a physiologically active agent, 1 to 30% by weight of oil, and 1 to 25% by weight of a tackifying resin, and having a water absorption 3 hours after of 55 to 240% and a water absorption 24 hours after of 240 to 450%. In the pressure-sensitive adhesive agent for skin of the preferable aspect, the physiologically active agent is preferably hydrophilic. In the pressure-sensitive adhesive agent for skin of the preferable aspect, the physiologically active agent is preferably a sphingolipid. In the pressure-sensitive adhesive agent for skin of the preferable aspect, the thermoplastic elastomer is preferably a hydrogenated styrene butadiene rubber.

The pressure-sensitive adhesive agent for skin of the invention described above can be used in various forms. For example, in addition to the form containing a base material as in a "pressure-sensitive adhesive sheet for skin" described later, the pressure-sensitive adhesive agent for skin of the invention can be used without using a base material by molding the same into a plate, a ring, a stick, or the like or can be used by charging the same in a tube or a bottle.

(Pressure-Sensitive Adhesive Sheet for Skin)

A pressure-sensitive adhesive sheet for skin of the invention contains a base material and a layer of a pressure-sensitive adhesive agent for skin formed at one side of the base material.

The layer of the pressure-sensitive adhesive agent for skin can be constituted by the same materials and the same ratio as in the pressure-sensitive adhesive agent for skin of the invention.

(Base Material)

As a base material, films, foam (foamed substance), fabrics (nonwoven fabrics, textiles, and knitted fabrics), and the like can be used. Among the above, from the viewpoint of softness, elasticity, moderate water vapor permeation properties, bacillus barrier properties, ease of wiping off dirt, and the like, films are preferable.

Specific examples of film materials include polyurethane, polyester, polyamide, polyethylene, polypropylene, an acrylic polymer, and an olefin copolymer. Among the above, polyurethane, polyester, and polyamide are preferable.

The thickness of the base material is preferably 5 to 150 μm and particularly preferably 10 to 100 μm.

The thickness of the layer of the pressure-sensitive adhesive agent for skin is preferably 0.1 to 2.5 mm and more preferably 0.3 to 2 mm. Since the thickness of the adhesive layer for skin is within the above-mentioned range, moderate adhesion strength is demonstrated when the pressure-sensitive adhesive sheet for skin is adhered to the skin, and excellent adaptability to the skin and a preferable water absorption can be achieved.

The shape of the pressure-sensitive adhesive sheet for skin of the invention may be selected as appropriate according to the intended use. As a specific shape, a circular shape, an elliptical shape, polygons, such as a triangle, a square, or a diamond, or the like can be mentioned. Moreover, the above-mentioned shapes may be combined preferably or a roll shape may be acceptable.

Methods for forming the layer of the pressure-sensitive adhesive agent for skin of the invention at one side of the base material are not particularly limited, and a method including rolling the adhesive agent in the shape of a sheet, and adhering the base material thereto, a method including pressing out the adhesive agent directly to the base material, and pressing, and the like can be mentioned. Among the above, the method including rolling the adhesive agent in the shape of a sheet, and adhering the base material thereto is preferable.

In the pressure-sensitive adhesive sheet for skin of the invention, the water absorption 3 hours after and the water absorption 24 hours after need to be 55 to 240% and 240 to 450%, respectively and more preferably 60 to 200% and 250 to 420%, respectively. Since the water absorption is within the above-mentioned range, skin troubles during adhesion decrease and prolonged adhering can be achieved.

Moreover, in the pressure-sensitive adhesive sheet for skin of the invention, the swelling ratio 3 hours after is 110% or lower and the swelling ratio 24 hours after is preferably 130% or lower. Since the swelling ratio is within the above-mentioned range, the pressure-sensitive adhesive agent for skin can maintain the shape even after water absorption and leaves no adhesive residue even after separation.

The pressure-sensitive adhesive sheet for skin of the invention preferably has a flexibility of 10 to 50 mm/20 mm. Since the flexibility is within the above-mentioned range, the adaptability to the skin is high and unpleasantness hardly arises during adhesion.

The pressure-sensitive adhesive sheet for skin of the invention has a visible light transmittance of preferably 2.5% or more and more preferably 5.0% or more. Since the visible light transmittance is within the above-mentioned range, the appearance when the pressure-sensitive adhesive sheet for skin is adhered to the skin improves and the state of water absorption or the skin can be easily observed while the pressure-sensitive adhesive sheet for skin is being adhered to the skin. Thus, a suitable time for replacement can be confirmed without separating the adhered pressure-sensitive adhesive sheet for skin and leakage of moisture or unnecessary replacement can be prevented.

(Pressure-Sensitive Adhesive Sheet for Face Plate of Ostomy Appliance and Face Plate for Ostomy Appliance)

The pressure-sensitive adhesive sheet for skin of the invention containing a base material and a layer of the pressure-sensitive adhesive agent for skin formed at one side of the base material is suitable as a pressure-sensitive adhesive sheet for face plate of ostomy appliance. More specifically, the pressure-sensitive adhesive sheet for skin of the invention is suitable as a pressure-sensitive adhesive sheet for adhering and fixing the face plate of ostomy appliance (ostomy pouch) to the surrounding of a stoma.

The face plate for ostomy appliance of the invention contains the pressure-sensitive adhesive sheet for face plate of ostomy appliance.

The pressure-sensitive adhesive sheet for face plate of ostomy appliance of the invention can be used for any of ostomy appliances of a one-piece type and a two-piece type. The face plate can be constituted by former methods in such a manner as to fit the appliance of each type. More specifically, in the case of a one-piece type, an opening of an ostomy pouch may be bonded to the base material side of the pressure-sensitive adhesive sheet for skin. In the case of a two-piece type, a flange for engagement or adhesion may be attached to the base material side of the pressure-sensitive adhesive sheet for skin.

The pressure-sensitive adhesive sheet for face plate of ostomy appliance of the invention preferably has a convex shape on the surface adhering to the skin (surface opposite to the base material).

With a so-called convex-type face plate of ostomy appliance having a convex shape on the surface adhering to the skin of the pressure-sensitive adhesive sheet, when the height of a stoma is low or when the skin surrounding the stoma has wrinkles or hollows, the adhesiveness between the skin and the face plate can be increased to prevent leakage of excrement. In particular, when the pressure-sensitive adhesive sheet for skin having high adaptability and suitable water absorption properties of the invention and the convex shape are combined, more excellent adhesiveness to the skin can be secured.

The convex surface projects to the outside by preferably 1 to 15 mm and more preferably 2 to 10 mm relative to the adhesion surface which is not shaped into a convex. The convex surface forms a convex surface in a circle having a diameter in the range of preferably 25 to 120 mm and more preferably 50 to 90 mm.

Methods for forming the convex shape on the surface adhering to the skin of the pressure-sensitive adhesive sheet are not particularly limited and former methods, such as a method for pressing a plastic ring against the pressure-sensitive adhesive sheet for face plate of ostomy appliance from the side opposite to the adhesion surface, a method for embedding a plastic ring into the layer of the pressure-sensitive adhesive agent for skin, and a method for forming the face plate central part into a convex shape by pressing with a die, can be used.

It is preferable in the pressure-sensitive adhesive sheet for face plate of ostomy appliance of the invention that a stoma inserting hole be formed in the central part and a base be not present in the surrounding of the hole.

The region in which the base material is not provided is within preferably 40 mm and more preferably 25 mm from the outer peripheral edge of the stoma inserting hole. Thus, by not providing the base material in the surrounding of the stoma inserting hole, the shape or dimension of the hole can be easily changed with fingers without using scissors, and thus a face plate hole can be adjusted to closely fit the shape of the stoma. Since the pressure-sensitive adhesive agent for skin of the invention is soft, the hole diameter is easily adjusted by a hand, and, after adhesion, high adhesiveness to the skin can be achieved.

Methods for forming the stoma inserting hole are not particularly limited.

In the pressure-sensitive adhesive sheet for face plate of ostomy appliance of the invention, the stoma inserting hole is formed in the central part and the base material surrounding the hole may have a fragile portion. The fragile portion has a physical strength lower than that of the base material of portions other than the fragile portion, is more likely to deform, and is softer than portions other than the fragile portion.

The region of the fragile portion is within preferably 40 mm and more preferably 25 mm from the outer peripheral edge of the stoma inserting hole. Thus, by forming the fragile portion in the base material surrounding the stoma inserting hole, the shape or dimension of the opening can be easily changed with fingers without using scissors, and thus a face plate hole can be adjusted to closely fit the shape of the stoma. Since the pressure-sensitive adhesive agent for skin of the invention is soft, the hole diameter is easily adjusted by a hand, and, after adhesion, high adhesiveness to the skin can be achieved.

In an aspect in which the fragile portion is provided in the base material surrounding the stoma inserting hole, outflow of the pressure-sensitive adhesive agent for skin in the surrounding of the hole hardly occurs and adhesiveness between the inside of a pouch and the face plate can be prevented, compared with an aspect in which the base material is not provided in the surrounding of the stoma inserting hole.

Examples of methods for providing the fragile portion in the base material surrounding the stoma inserting hole include a method for partially forming a slit or a hole in the base material surrounding the hole, a method for subjecting the base material surrounding the hole to embossment or the like, and a method for constituting the base material surrounding the hole with a material softer than materials for other portions.

The face plate having a convex shape on the surface adhering to the skin and having no base material in the surrounding of the hole or having a fragile portion in a base material surrounding the hole achieves higher adhesiveness and no leakage of excrement when combined with excellent adhesiveness in the pressure-sensitive adhesive agent for skin of the invention.

EXAMPLES

Hereinafter, the present invention will be described in more detail with reference to Examples, but is not limited thereto. The properties of the pressure-sensitive adhesive agent for skin and the pressure-sensitive adhesive sheet for skin were evaluated by the following methods.

[Water Absorption]

A test piece having a diameter of 30 mm was extracted from a pressure-sensitive adhesive agent for skin or a pressure-sensitive adhesive sheet for skin, and the weight of the test piece was measured. The test piece was immersed in physiological saline (0.9% aqueous NaCl solution), and was allowed to stand still in a 37° C. thermostatic bath. The weight of the test piece was measured 3 hours and 24 hours after immersion, and the water absorption was determined by the following equation.

With respect to the pressure-sensitive adhesive agent for skin, the thickness of the test piece was set to 1.5 mm.

$$\text{Water absorption (\%)} = [(\text{Test piece weight after immersion} - \text{Test piece weight before immersion})/\text{Test piece weight before immersion}] \times 100$$

[Swelling Ratio]

A test piece having a diameter of 30 mm was extracted from a pressure-sensitive adhesive agent for skin or a pressure-sensitive adhesive sheet for skin. Then, the test piece was immersed in physiological saline (0.9% aqueous NaCl solution), and was allowed to stand still in a 37° C. thermostatic bath. The maximum diameter in two directions perpendicular to each other is measured 3 hours and 24 hours after immersion, the average value is defined as the diameter after water absorption, and the swelling ratio is calculated by the following equation.

With respect to the pressure-sensitive adhesive agent for skin, the thickness of the test piece is set to 1.5 mm.

$$\text{Swelling ratio (\%)} = (\text{Test piece diameter after water absorption (mm)}/\text{Test piece diameter before water absorption (30 mm)}) \times 100$$

[Flexibility]

The flexibility of a pressure-sensitive adhesive agent for skin and a pressure-sensitive adhesive sheet for skin is measured according to JIS L 1096 "Flexibility A method (45° cantilever method)". Specifically, the measurement is performed as follows.

Three test pieces of 20 mm×80 mm are prepared from the pressure-sensitive adhesive agent for skin or the pressure-sensitive adhesive sheet for skin, and were allowed to stand still under an environment of a temperature of 23° C. and a humidity of 65% for 1 hour. Thereafter, the short side of the test pieces was placed according to the scale baseline on a level stand one end of which has a 45° inclined plane and which has a smooth surface. Next, the test pieces are made to gently slide in the direction toward the inclined plane. Then, when the center point of one end of the test pieces touches the inclined plane of the level stand, the position of the other end of the test pieces is determined by a scale.

The flexibility is indicated by the length (mm) in which the test pieces moved. The front and back surfaces of the three test pieces were measured, and the average value is calculated.

With respect to the pressure-sensitive adhesive agent for skin, the thickness of the test piece is set to 1.5 mm.

[Visible Light Transmittance]

The transmittance of light in the wavelength of 550 nm is measured with a spectrophotometer.

With respect to the pressure-sensitive adhesive agent for skin, the thickness of the test piece is set to 1.5 mm.

[Skin Adhesion Evaluation]
[(1): Feeling of Adhesion]

A test piece having a width of 25 mm×a length of 50 mm is extracted from a pressure-sensitive adhesive agent for skin or a pressure-sensitive adhesive sheet for skin, and adhered to the abdomen of subjects. The feeling of adhesion is evaluated based on three grades in accordance with the degree of irritation or unpleasantness that the subjects feel until 24 hours have passed after adhesion (O: Irritation or unpleasantness hardly arises. Δ: Irritation or unpleasantness slightly arises. x: Strong irritation or unpleasantness arises.).

[Skin Adhesion Evaluation]
[(2): State after Adhesion]

The state of the test piece after 24 hours of adhesion is observed, and evaluated based on three grades in accordance with the degree of deformation or wrinkles, separation or floating, and the flow of the pressure-sensitive adhesive agent for skin (O: Hardly occurs. Δ: Slightly occurs. x: Remarkably occurs).

Example 1A

A hydrogenated styrene-butadiene rubber (manufactured by JSR Corporation) as a thermoplastic elastomer, polyisobutylene (manufactured by Nippon Oil Corporation, trade name: "HIMOL 6H") as a softener, and a liquid paraffin as oil are charged in a pressurization kneader, and then pressurized and mixed until the mixture becomes sufficiently uniform.

Next, sodium carboxymethylcellulose (manufactured by Nippon Paper Chemicals Co., Ltd) and pectin as a hydrophilic polymer compound, Type 2 ceramide as a physiologically active agent, and an alicyclic saturated hydrocarbon resin (manufactured by Arakawa Chemical Industries, Ltd., trade name "ARCON P-100") as a tackifying agent are added, mixed to be uniform, and rolled to have a thickness of 1.5 mm, thereby obtaining a pressure-sensitive adhesive agent for skin 1A. The blending amount of each ingredient is shown in Table 1.

Example 1B

To the pressure-sensitive adhesive agent for skin obtained in Example 1, a polyurethane film base material (Weight per unit area of 15 g/m$^2$ and Thickness of 15 μm) is laminated, thereby obtaining a pressure-sensitive adhesive sheet for skin 1B.

The properties of the pressure-sensitive adhesive sheet for skin were evaluated. The results are shown in Table 1.

Examples 2B to 4B

Pressure-sensitive adhesive agents for skin 2A to 4A were obtained in the same manner as in Example 1, except changing the amount of each ingredient as shown in Table 1. Pressure-sensitive adhesive sheets for skin 2B to 4B for skin were obtained in the same manner as in Example 1B using the pressure-sensitive adhesive agents for skin. The results of evaluating the properties are shown in Table 1 (Here, the evaluation results of the water absorption, swelling ratio, flexibility, and skin adhesion shown in Table 1 are measurement values as a pressure-sensitive adhesive sheet for skin.). As a base material, a polyethylene film was used in Examples 2B and 3B and a polyurethane film was used in Example 4B.

Comparative Examples C1B to C3B)

A pressure-sensitive adhesive sheet for skin C1B was produced using an EMA (ethylene-methyl acrylate copolymer) film as the base material in place of the pressure-sensitive adhesive sheet for skin of the invention and using an adhesive agent having the composition shown in Table 1, and the properties thereof were evaluated.

Moreover, the properties of pressure-sensitive adhesive sheets for skin C2B and C3B for use in commercial face plates for ostomy appliance were evaluated (Comparative Example C2B: "Varicare Natura Flange" manufactured by Conva Tec Inc., Comparative Example C3B: "Assura self plate clearance" manufactured by Coloplast).

TABLE 1

| | Examples | | | | | Comparative Examples | | |
|---|---|---|---|---|---|---|---|---|
| | 1A | 1B | 2B | 3B | 4B | C1B | C2B | C3B |
| Composition of pressure-sensitive adhesive agent (% by weight) (*1) Thermoplastic elastomer | | | | | | | | |
| HSBR | 10.3 | 10.3 | 11.2 | 10.6 | — | — | — | — |
| SIS | — | — | — | — | 11.7 | — | — | — |
| Hydrophilic polymer compound | | | | | | | | |
| CMC·Na | 23.2 | 23.2 | 23.2 | 21.9 | 21.9 | — | — | — |
| Pectin | 17.6 | 17.6 | 17.7 | 22.2 | 22.2 | 26.8 | — | — |
| Karaya gum | — | — | — | — | — | 16.4 | — | — |
| Gelatin | — | — | — | — | — | 4.4 | — | — |
| Guar gum | — | — | — | — | — | 4.4 | — | — |
| Softener | | | | | | | | |
| Polyisobutylene | 30.0 | 30.0 | 28.1 | 26.5 | 25.0 | 40.0 | — | — |
| Oil | | | | | | | | |
| Liquid paraffin | 6.8 | 6.8 | 4.8 | 4.6 | 5.0 | — | — | — |
| Physiologically active agent | | | | | | | | |
| Ceramide | 0.3 | 0.3 | 0.3 | 0.3 | 0.3 | — | — | — |
| Tackifying agent | | | | | | | | |
| Aliphatic saturated hydrocarbon resin | 11.8 | 11.8 | 14.7 | 13.9 | 13.9 | — | — | — |

TABLE 1-continued

|  | Examples | | | | | Comparative Examples | | |
| --- | --- | --- | --- | --- | --- | --- | --- | --- |
|  | 1A | 1B | 2B | 3B | 4B | C1B | C2B | C3B |
| Other controlling agents | | | | | | | | |
| Butyl rubber | — | — | — | — | — | 4.4 | — | — |
| Silica | — | — | — | — | — | 3.6 | — | — |
| Pressure-sensitive adhesive agent or adhesive sheet | | | | | | | | |
| Thickness of pressure-sensitive adhesive agent (mm) | 1.5 | 1.5 | 1.5 | 1.5 | 1.5 | 1.9 | About 1.9 | About 1.5 |
| Thickness of base material (mm) | — | 15 | 70 | 70 | 30 | 100 | 80 | 70 |
| Water absorption (%) | | | | | | | | |
| 3 hours after | 165 | 76 | 117 | 113 | 134 | 170 | 244 | 48 |
| 24 hours after | 314 | 276 | 399 | 364 | 418 | 464 | Collapse | 230 |
| Swelling ratio (%) | | | | | | | | |
| 3 hours after | 119 | 105 | 107 | 108 | 110 | 109 | 112 | 103 |
| 24 hours after | 134 | 115 | 128 | 125 | 130 | 132 | Collapse | 108 |
| Flexibility (mm/20 mm) | 26.7 | 36.7 | 43.7 | 47.3 | 40.0 | 43.3 | 55.0 | 53.3 |
| Evaluation of skin adhesion | | | | | | | | |
| Feeling of adhesion | ○ | ○ | ○ | ○ | ○ | X | X | Δ |
| State after adhesion | ○ | ○ | ○ | ○ | ○ | X | X | ○ |

(*1): HBSR: Hydrogenated styrene-butadiene rubber SIS: Styrene-isoprene-styrene block copolymer CMC•Na: Sodium carboxymethylcellulose As a result of the above-described evaluation, the pressure-sensitive adhesive sheet for skin of the invention hardly causes irritation or unpleasantness during adhesion, hardly causes wrinkles, separation, or the like of the test pieces, maintains shape retention properties without causing flow of the pressure-sensitive adhesive agent for skin, and leaves no residue of the pressure-sensitive adhesive agent for skin on the skin after separation. It is considered that this is because characteristic aggregation properties, softness, and water absorption properties of the pressure-sensitive adhesive agent for skin are obtained due to the composition balance of the pressure-sensitive adhesive agent for skin of the invention, and preferable adaptability, adhesiveness, and the like to the skin are demonstrated by these properties.

In contrast, in the pressure-sensitive adhesive sheets for skin of Comparative Examples, the pressure-sensitive adhesive agents for skin caused deformation or flow, and moreover the pressure-sensitive adhesive agents for skin that absorbed water once were dried to become hard, causing irritation or unpleasantness during adhesion.

Example 1C

Figure 1:
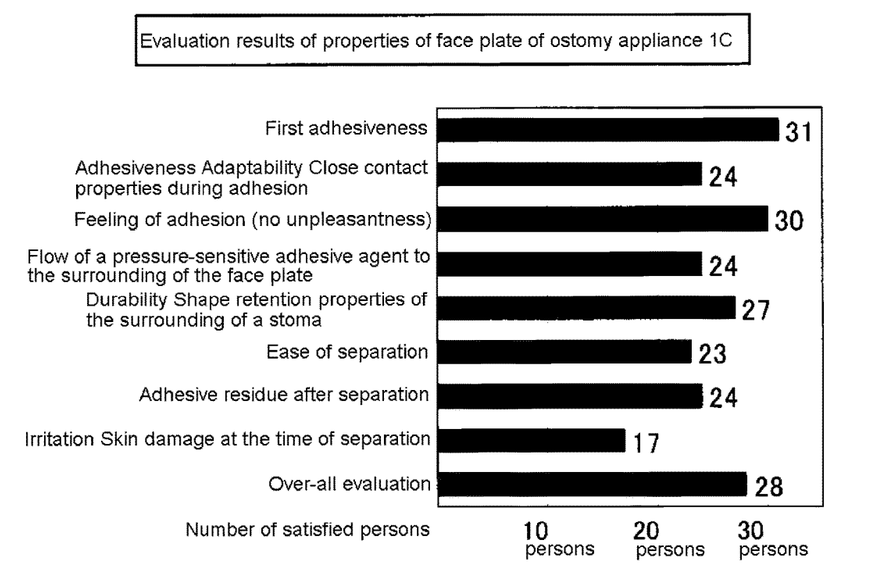
FIG. 1 is a graph showing the evaluation results of the face plate of ostomy appliance of the invention by stoma holders.

An approximately round-shaped face plate of ostomy appliance 1C was cut out from the pressure-sensitive adhesive sheet for skin obtained in Example 1B, and a two-piece fitting type ostomy appliance using the face plate 1C was produced by former methods. 38 stoma holders evaluated various properties when the face plate of ostomy appliance 1C was used in place of former products. The results are shown in FIG. 1. The numbers indicated in FIG. 1 are the numbers of the stoma holders, who judged that the properties of the face plate of ostomy appliance 1C of the invention are satisfactory, out of the 38 stoma holders who participated in the evaluation.

The former products that the 38 stoma holders used were two-piece fitting type ostomy appliances, and the pressure-sensitive adhesive sheet of the face plate has the following composition and the water absorption properties.

[Composition of the Former Pressure-Sensitive Adhesive Agent]

The former pressure-sensitive adhesive agent contains 51% by weight of hydrophilic polymer compounds containing karaya gum, pectin, alginic acid salt, gelatin, and guar gum, 36% by weight of a softener containing polyisobutylene, 4.4% by weight of a tackifying resin containing alicyclic saturated hydrocarbon resin, and 4.4% by weight of butyl rubber and 4.2% by weight of silica as other controlling agents.

[Water Absorption of the Former Pressure-Sensitive Adhesive Agent]

The water absorption 3 hours after is 153% and the water absorption 24 hours after is 541%.

As is shown from the results of FIG. 1, the face plate of ostomy appliance of the invention is excellent in the adhesiveness (first adhesiveness) when the face plate is first adhered to the skin or the adhesiveness, feeling of adhesion, durability, or the like during adhesion compared with the former product, and moreover leaves no residue of the pressure-sensitive adhesive agent (adhesive residue) on the skin after separation and can be separated without applying damages to the skin, and thus is very satisfactory with all things considered. Accordingly, it can be said that the face plate of ostomy appliance of the invention causes very little skin irritation and can maintain or increase the physiological function (skin barrier function) of the skin even when used over a long period of time.

The invention claimed is:

1. A pressure-sensitive adhesive agent for skin, consisting of:
   5 to 20% by weight of a hydrogenated styrene-butadiene rubber,
   35 to 55% by weight of at least one hydrophilic polymer compound selected from the group consisting of sodium carboxymethyl cellulose, pectin, karaya gum, and gelatin,
   a softener component comprising a single softener of 25 to 30% by weight, wherein said single softener is selected from the group consisting of polyisobutylene, polyisoprene, polybutadiene, polybutene, styrene-isoprene rubber, ethylene-propylene rubber, styrene-ethylene-propylene rubber, and derivatives thereof, 0.05 to 3% by weight of a ceramide, 2 to 20% by weight of a mineral oil, 1 to 25% by weight of a tackifying resin comprising a petroleum resin, and optionally one or more components selected from the group consisting of:
- one or more thermoplastic elastomers, one or more hydrophilic polymers,
- one or more physiologically active agents selected from the group consisting of sphingolipid, urea, glycolic acid, amino acids and derivatives thereof, protein hydrolysates, mucopolysaccharides and derivatives thereof, a vitamin B group, ascorbic acids, retinoids, vitamin D, vitamin E and derivatives thereof, carotenoids, enzymes, coenzymes, and γ-oryzanol,
- one or more oils selected from the group consisting of vegetable oils, animal oils, and synthetic oils,
- one or more adhesiveness-imparting resins selected from the group consisting of aliphatic copolymers, aromatic copolymers, aliphatic-aromatic copolymers, alicyclic copolymers, coumarone-indene resins, terpene resins, terpene-phenol resins, rosin resins; (alkyl) phenol resins, xylene resins, and hydrogenated resins thereof, and one or more ingredients selected from the group consisting of powder and pH adjusters.

2. A pressure-sensitive adhesive sheet for skin, comprising:
a base material and a layer of the pressure-sensitive adhesive agent for skin according to claim 1.

3. A pressure-sensitive adhesive sheet for a face plate of ostomy appliance, comprising the pressure-sensitive adhesive sheet for skin according to claim 2.

4. The pressure-sensitive adhesive sheet for the face plate of ostomy appliance according to claim 3 wherein the pressure-sensitive sheet comprises a layer of a pressure-sensitive adhesive agent for skin having a surface adhering to a skin, the surface having a convex portion thereon.

5. A face plate of ostomy appliance, comprising a pressure-sensitive adhesive sheet for a face plate of ostomy appliance according to claim 3.

6. The pressure-sensitive adhesive agent for skin according to claim 1, wherein said pressure-sensitive adhesive agent has a water absorption 3 hours after of 55 to 240% and a water absorption 24 hours after of 240 to 450%; and has a swelling ratio 3 hours after of lower than or equal to 135% and a swelling ratio 24 hours after of lower than or equal to 145%; wherein % by weight is based on the total weight of the adhesive agent.

7. The pressure-sensitive adhesive sheet for skin according to claim 2, wherein said pressure-sensitive adhesive sheet has a water absorption 3 hours after of 55 to 240% and a water absorption 24 hours after of 240 to 450%; and has a swelling ratio 3 hours after of lower than or equal to 135% and a swelling ratio 24 hours after of lower than or equal to 145%; wherein % by weight is based on the total weight of the adhesive agent.

8. The pressure-sensitive adhesive agent for skin according to claim 6, wherein said pressure-sensitive adhesive agent has a water absorption 3 hours after of 60 to 200% and a water absorption 24 hours after of 250 to 420%.

9. The pressure-sensitive adhesive sheet for skin according to claim 7, wherein said pressure-sensitive adhesive sheet has a water absorption 3 hours after of 60 to 200% and a water absorption 24 hours after of 250 to 420%.

10. The pressure-sensitive adhesive agent for skin according to claim 1, wherein the tackifying resin comprising the petroleum resin is 11.8 to 25% by weight.

11. The pressure-sensitive adhesive sheet for skin according to claim 2, wherein the tackifying resin comprising the petroleum resin is 11.8 to 25% by weight.

12. The pressure-sensitive adhesive agent for skin according to claim 1, herein the mineral oil is 6.8 to 20% by weight.

13. The pressure-sensitive adhesive sheet for skin according to claim 2, wherein the mineral oil is 6.8 to 20% by weight.

14. A pressure-sensitive adhesive agent for skin, consisting of:
5 to 20% by weight of a hydrogenated styrene-butadiene rubber, 35 to 55% by weight of at least one hydrophilic polymer compound selected from the group consisting of sodium carboxymethyl cellulose, pectin, karaya gum, and gelatin, softener component consisting of at least one softener of 25 to 30% by weight, wherein said at least one softener is selected from the group consisting of polyisobutylene, polyisoprene, polybutadiene, polybutene, styrene-isoprene rubber, ethylene-propylene rubber, styrene-ethylene-propylene rubber, and derivatives thereof, 0.05 to 3% by weight of a ceramide, 2 to 20% by weight of a mineral oil, 1 to 25% by weight of a tackifying resin comprising a petroleum resin, and optionally one or more components selected from the group consisting of:
- one or more thermoplastic elastomers, one or more hydrophilic polymers,
- one or more physiologically active agents selected from the group consisting of sphingolipid, urea, glycolic acid, amino acids and derivatives thereof, protein hydrolysates, mucopolysaccharides and derivatives thereof, a vitamin B group, ascorbic acids, retinoids, vitamin D, vitamin E and derivatives thereof, carotenoids, enzymes, coenzymes, and γ-oryzanol,
- one or more oils selected from the group consisting of vegetable oils, animal oils, and synthetic oils,
- one or more adhesiveness-imparting resins selected from the group consisting of aliphatic copolymers, aromatic copolymers, aliphatic-aromatic copolymers, alicyclic copolymers, coumarone-indene resins, terpene resins, terpene-phenol resins, rosin resins; (alkyl) phenol resins, xylene resins, and hydrogenated resins thereof, and
- one or more ingredients selected from the group consisting of powder and pH adjusters.

15. A pressure-sensitive adhesive agent for skin, consisting of:
5 to 20% by weight of a hydrogenated styrene-butadiene rubber, 35 to 55% by weight of at least one hydrophilic polymer compound selected from the group consisting of sodium carboxymethyl cellulose, pectin, karaya gum, and gelatin, a softener component consisting of a single softener of 25 to 30% by weight, wherein said single softener is selected from the group consisting of polyisobutylene, polyisoprene, polybutadiene, polybutene, styrene-isoprene rubber, ethylene-propylene rubber, styrene-ethylene-propylene rubber, and derivatives thereof, 0.05 to 3% by weight of a ceramide,
2 to 20% by weight of a mineral oil,
1 to 25% by weight of a tackifying resin comprising a petroleum resin, and
optionally one or more components selected from the group consisting of:
- one or more thermoplastic elastomers, one or more hydrophilic polymers,
- one or more physiologically active agents selected from the group consisting of sphingolipid, urea, glycolic acid, amino acids and derivatives thereof, protein hydrolysates, mucopolysaccharides and derivatives thereof, a vitamin B group, ascorbic acids, retinoids, vitamin D, vitamin E and derivatives thereof, carotenoids, enzymes, coenzymes, and γ-oryzanol,
- one or more oils selected from the group consisting of vegetable oils, animal oils, and synthetic oils,
- one or more adhesiveness-imparting resins selected from the group consisting of aliphatic copolymers, aromatic copolymers, aliphatic-aromatic copolymers, alicyclic copolymers, coumarone-indene resins, terpene resins, terpene-phenol resins, rosin resins; (alkyl) phenol resins, xylene resins, and hydrogenated resins thereof, and
- one or more ingredients selected from the group consisting of powder and pH adjusters.

16. A pressure-sensitive adhesive agent for skin, consisting of:
5 to 20% by weight of a hydrogenated styrene-butadiene rubber,
35 to 55% by weight of at least one hydrophilic polymer compound selected from the group consisting of sodium carboxymethyl cellulose, pectin, karaya gum, and gelatin,
a softener component consisting of softeners of 25 to 30% by weight, wherein said softeners are respectively selected from the group consisting of polyisobutylene, polyisoprene, polybutadiene, polybutene, styrene-isoprene rubber, ethylene-propylene rubber, styrene-ethylene-propylene rubber, and derivatives thereof,
0.05 to 3% by weight of a ceramide,
2 to 20% by weight of a mineral oil,
1 to 25% by weight of a tackifying resin comprising a petroleum resin, and
optionally one or more components selected from the group consisting of:
- one or more thermoplastic elastomers, one or more hydrophilic polymers,
- one or more physiologically active agents selected from the group consisting of sphingolipid, urea, glycolic acid, amino acids and derivatives thereof, protein hydrolysates, mucopolysaccharides and derivatives thereof, a vitamin B group, ascorbic acids, retinoids, vitamin D, vitamin E and derivatives thereof, carotenoids, enzymes, coenzymes, and γ-oryzanol,
- one or more oils selected from the group consisting of vegetable oils, animal oils, and synthetic oils,
- one or more adhesiveness-imparting resins selected from the group consisting of aliphatic copolymers, aromatic copolymers, aliphatic-aromatic copolymers, alicyclic copolymers, coumarone-indene resins, terpene resins, terpene-phenol resins, rosin resins; (alkyl) phenol resins, xylene resins, and hydrogenated resins thereof, and
- one or more ingredients selected from the group consisting of powder and pH adjusters.

* * * * *